United States Patent [19]

Gladwin

[11] 4,254,288

[45] Mar. 3, 1981

[54] CATALYTIC DEHYDROGENATION

[75] Inventor: Keith Gladwin, Chesterfield, England

[73] Assignee: Coalite Group Limited, England

[21] Appl. No.: 55,300

[22] Filed: Jul. 6, 1979

[51] Int. Cl.$^3$ .............................................. C07C 37/06
[52] U.S. Cl. .................................... 568/652; 585/442; 568/650; 568/740; 568/653; 260/696
[58] Field of Search .............. 568/650, 652, 740, 653; 585/442; 260/696

[56] References Cited

U.S. PATENT DOCUMENTS

| | | | |
|---|---|---|---|
| 3,819,719 | 6/1974 | McKague et al. | 568/652 |
| 3,935,282 | 1/1976 | Kudo et al. | 568/740 |
| 4,046,816 | 9/1977 | Müller | 568/650 X |

OTHER PUBLICATIONS

Charonnat et al., Bull. Soc. Chim., France (1949) 209–211.

*Primary Examiner*—Bernard Helfin
*Attorney, Agent, or Firm*—Burmeister, York, Palmatier, Hamby & Jones

[57] ABSTRACT

A method of producing an aromatic compound comprises dehydrogenating a compound having a six-membered carbocyclic ring in the molecule, the ring having a degree of saturation greater than that of a benzene ring, the dehydrogenation being carried out in the presence of a catalyst system comprising elemental palladium together with sodium carbonate and sulphur. The compound to be dehydrogenated may be a substituted cyclohexane. When the substituted cyclohexane is an alkoxycyclohexanol, the aromatic compound produced is an alkoxy phenol. In particularly useful aspect of the invention the substituted cyclohexane is a 2-alkoxycyclohexanol, the aromatic compound produced being an ortho-alkoxy phenol.

19 Claims, No Drawings

CATALYTIC DEHYDROGENATION

The present invention relates to the dehydrogenation of compounds having a six-membered carbocyclic ring in the molecule, the ring having a degree of saturation greater than that of a benzene ring.

BACKGROUND ART

It is known to dehydrogenate substituted cyclohexanes to produce the corresponding aromatic compounds using a platinum catalyst, usually a platinum-on-carbon catalyst. An example of such a dehydrogenation is the dehydrogenation of a 2-alkoxycyclohexanol to produce an orthoalkoxyphenol.

DISCLOSURE OF THE INVENTION

It has now been discovered that improved yields and/or greater selectivity can be obtained in the dehydrogenation of substituted cyclohexanes by the use of a catalyst system comprising elemental palladium together with sulphur and sodium carbonate. In general, it is envisaged that this catalyst system would be useful in the dehydrogenation of compounds having a six-membered carbocyclic ring in the molecule, the ring having a degree of saturation greater than that of a benzene ring.

Accordingly the present invention provides a method of producing an aromatic compound, comprising dehydrogenating a compound having a six-membered carbocyclic ring in the molecule, the ring having a degree of saturation greater than that of a benzene ring, the dehydrogenation being carried out in the presence of a catalyst system comprising elemental palladium together with sodium carbonate and sulphur.

The compound to be dehydrogenated may be a substituted cyclohexane. The substituted cyclohexane may be an alkoxycyclohexanol, the aromatic compound produced being an alkoxyphenol. The alkoxy cyclohexanol may be a 2-alkoxy cyclohexanol, the aromatic compound produced being an ortho-alkoxyphenol.

Aromatic compounds produced by the method of the invention are useful as intermediates. In particular the 2-alkoxycyclohexanol may be 2-isopropoxycyclohexanol, the aromatic compound produced being o-isopropoxyphenol, which is useful as an intermediate in the active ingredient in the insecticidal compositions marketed under the trade names "Baygon" and "Propoxur".

The dehydrogenation is preferably carried out in a solvent, conveniently under reflux.

The palladium in the catalyst system is conveniently provided by a palladium-on-carbon catalyst, i.e. porous carbon having elemental palladium deposited therein.

The palladium-on-carbon catalyst preferably comprises 2.8 to 3.2% palladium and is preferably present in an amount of up to 10%, more preferably up to 5%, by weight.

The sulphur may be in the form of elemental sulphur or a sulphur-containing covalent compound e.g. diphenyl sulphide or thiodipropionic acid.

The sulphur is preferably present in the reaction system in an amount of 18 to 30 ppm (based on the reaction system), more preferably 20 to 24 ppm, although the preferred amount of sulphur depends to some extent on the amount and form of the palladium present.

It will be appreciated that by "the reaction system" we mean the system consisting of the compound to be dehydrogenated, the catalyst system, any solvent or other reaction medium present and any reaction products.

The sodium carbonate is preferably added to the compound to be dehydrogenated and any reaction medium as a solid, more preferably an anhydrous sodium carbonate.

The sodium carbonate is preferably present in the reaction system in an amount (calculated as anhydrous $Na_2CO_3$) of 0.5 to 1.5% by weight based upon the compound to be dehydrogenated.

EXAMPLES

Examples 1 to 17.

Examples 1 to 11 are comparative examples and Examples 12 to 17 illustrate the invention. Reaction conditions and results are given in a Table following the description of the examples.

In each example except Examples 6 and 7 a mixture of 2-isopropoxy cyclohexanol (21 PC) and diphenyl (as solvent) was introduced into a reaction vessel. In Examples 6 and 7 21 PC alone was introduced into the reaction vessel. The catalyst was added to the reaction vessel. In Examples 1 to 6 and 12 to 17, the catalyst was a palladium-on-carbon (porous charcoal) catalyst. In Examples 7 to 11, the catalyst was a platinum-on-carbon (porous charcoal) catalyst. The palladium on-carbon catalyst comprised 3% by weight palladium. The platinum-on-carbon catalyst comprised 5% by weight platinum. Then, in Example 12 to 17, a solution of diphenyl sulphide in further of the 2-isopropoxy cyclohexanol was added to the reaction vessel. Next, in all examples, powdered sodium carbonate (anhydrous) or powdered potassium carbonate (anhydrous) was added to the contents of the reaction vessel to form the reaction system.

The volume ratio of 2-isopropoxy cyclohexanol to diphenyl (if any) and the concentration of sulphur (as diphenyl sulphide) in the resulting reaction system are given in the Table. The concentration of $Na_2CO_3$ or $K_2CO_3$ in the resulting reaction system was 1% by weight. The Table gives the amount of catalyst present in the reaction system as a percentage by weight.

The reaction system was refluxed, at the temperature stated in the Table, whilst a stream of nitrogen was passed through the system. When hydrogen ceased to be produced, the dehydrogenation reaction was considered to be completed and the reaction system was cooled and treated with sodium hydroxide to extract a product comprising: o-isopropoxyphenol and, as impurities, o-isopropoxycyclohexanol and various by-products.

The carbon of the catalysts was as follows:

Examples 1 to 6 and 12 to 17—Johnson Matthey JM 87L porous charcoal.

Example 8—Johnson Matthey Type 16 porous charcoal.

Examples 9, 10 and 12—Johnson Matthey CDZ 11 porous charcoal.

Example 11—Johnson Matthey RS134 porous charcoal.

TABLE

| Ex. No. | Ratio of Diphenyl to 21PC (by volume) | Catalyst and amount (%) | Carbonate used | Amount of Sulphur added | Refluxing Temperature °C. | Reaction Time (hrs) |
|---|---|---|---|---|---|---|
| 1 | 1:1 | Pd/C | $K_2CO_3$ | 0 | 216-24 | 48 |

TABLE-continued

| | | | | | | |
|---|---|---|---|---|---|---|
| 2 | 1:1 | Pd/C 1.7 | Na₂CO₃ | 0 | 210 | 48 |
| 3 | 1:1 | Pd/C 1.7 | Na₂CO₃ | 0 | 210 | 48 |
| 4 | 1:1 | Pd/C 1.7 | Na₂CO₃ | 0 | 210 | 48 |
| 5 | 2:1 | Pd/C 1.7 | Na₂CO₃ | 0 | 230 | 48 |
| 6 | 0:1 (no diphenyl) | Pd/C 1.7 | Na₂CO₃ | 0 | 198 | 48 |
| 7 | 0:1 | Pt/C 2 | None | 0 | 200 | 32 |
| 8 | 1:1 | Pt/C 1 | None | 0 | 200 | 32 |
| 9 | 1:1 | Pt/C 1 | None | 0 | 210 | 36 |
| 10 | 1:1 | Pt/C 1 | None | 0 | 212 | 24 |
| 11 | 1:1 | Pt/C 1 | Na₂CO₃ | 0 | 212 | 36 |
| 12 | 1:1 | Pd/C 1 | Na₂CO₃ | 6 | 21-225 | 24 |
| 13 | 1:1 | Pd/C 1.7 | Na₂CO₃ | 12 | 210-16 | 48 |
| 14 | 1:1 | Pd/C 1.7 | Na₂CO₃ | 12 | 216-20 | 33 |
| 15 | 1:1 | Pd/C 1.7 | Na₂CO₃ | 18 | 210-20 | 18 |
| 16 | 1:1 | Pd/C 1.7 | Na₂CO₃ | 18 | 210-20 | 25 |
| 17 | 1:1 | Pd/C 1.7 | Na₂CO₃ | 24 | 210-20 | 21 |

| % Crude Yield | % Purity | % Actual Yield | ANALYSIS OF IMPURITIES | | | | |
|---|---|---|---|---|---|---|---|
| | | | Phenol | Catechol | Diphenyl | 21PC | Unknowns |
| 29.0 | — | — | — | — | — | — | — |
| 50 | 84 | 42 | 12.5 | 1.0 | — | — | 2.6 |
| 18.7 | 96.2 | 18 | 2.2 | 1.6 | — | — | — |
| 50 | 89.8 | 44.9 | 6.7 | 2.3 | — | — | 1.2 |
| 37 | 82 | 30.7 | 15.7 | 1.4 | — | — | 0.8 |
| 33 | — | — | — | — | — | — | — |
| | | | — | — | — | 50 | 30 |
| | | | — | — | — | 64 | 14 |
| | | | — | — | — | 15 | 25 |
| | | | — | — | — | 50 | — |
| | | | — | — | — | 18 | 16 |
| 56.1 | 94.3 | 52.8 | 3.4 | 1.6 | — | — | 0.7 |
| 63.4 | 87 | 55.0 | 12.2 | 0.8 | — | — | 0.1 |
| 80 | 93 | 74 | 4.8 | 0.8 | — | — | 1.4 |
| 82.3 | 95.6 | 78.7 | 3.2 | 1.2 | — | — | — |
| 76 | 95.5 | 72.5 | 3.8 | 0.7 | — | — | — |
| 85.2 | 97.8 | 83 | 1.4 | 0.4 | 0.2 | 0.2 | — |

The stated amounts of impurities are percentages based upon all components of the reaction mixture excluding diphenyl.

In each of Examples 7 to 11 (using platinum-on-carbon catalysts), a substantial loss of weight of the reaction system occurred during the refluxing, indicating breakdown of the 21PC into gaseous hydrocarbons.

It was found that adding sulphur to the reaction system comprising of the platinum-on-carbon catalysts completely poisoned the platinum and no reaction occurred.

Example 18

In this example o-isopropoxyphenol produced in accordance with the invention was isolated by distillation.

2-isopropoxycyclohexanol (316 g), diphenyl (316 g) and Pd/C catalyst (10.6 g) were added to a dehydrogenator together with sodium carbonate (3.16 g) and diphenyl sulphide (equiv. to 24 ppm S). The content of the reactor were brought to reflux and maintained at reflux for 24 hrs. Over this period 144 liters of hydrogen and off gases are evolved.

The reaction mixture was filtered (to remove solid material) at 80° C. and the filtrate collected (578.5 g). This filtrate was fractionated through a 50-plate column at 17 mm.Hg at 10 g/hr. offtake giving the following fractions:

| 1. | Fronts | Largly Phenol | 21g |
|---|---|---|---|
| 2. | Main Distilcate | B.p. 106° C. | 252.3g |

The main distillate had the following analysis:

| Phenol | 0.14% |
|---|---|
| 2 IPC | 2.3% |
| Catechol | 0.1% |
| Unknowns | 0.08% |

Assuming no further impurities the main distillate was 97.4% pure and the yield of o-isopropoxyphenol was 81% based upon 2-isopropoxycyclohexanol.

The fractionation residue after an Engler distillation was re-usable as solvent for further dehydrogenations.

What I claim is:

1. In the method of dehydrogenating a compound having a six-membered carbocyclic ring in the molecule, the ring having a degree of saturation greater than that of a benzene ring, wherein said compound is dehydrogenated using a dehydrogenation catalyst to produce the corresponding aromatic compounds, the improvement which comprises heating said compound at a temperature and time sufficient to effect dehydrogenation to produce the corresponding aromatic compound in the presence of a catalyst system comprising elemental palladium together with sodium carbonate and elemental sulphur or an organic co-valent sulphur compound.

2. A method according to claim 1, wherein the compound to be dehydrogenated is a substituted cyclohexane.

3. A method according to claim 2, wherein the substituted cyclohexane is an alkoxycyclohexanol, the aromatic compound produced being an alkoxyphenol.

4. A method according to claim 3, wherein the alkoxycyclohexanol is a 2-alkoxycyclohexanol, the aromatic compound produced being an ortho-alkoxy phenol.

5. A method according to claim 4, wherein the 2-alkoxycyclohexanol is 2-isopropoxycyclohexanol, the aromatic compound produced being o-isopropoxyphenol.

6. A method according to claim 1, wherein the dehydrogenation is carried out in a solvent.

7. A method according to claim 1, wherein the palladium in the catalyst system is provided by a palladium-on-carbon catalyst.

8. A method according to claim 7, wherein the palladium-on-carbon catalyst comprises 2.8 to 3.2% by weight palladium.

9. A method according to claim 7 or 8, wherein the palladium-on-carbon catalyst is present in the reaction system in an amount of up to 10% by weight.

10. A method according to claim 9, wherein the palladium-on-carbon catalyst is present in the reaction system in an amount of up to 5% by weight 11. A method according to claim 1, wherein the sulphur is in the form of elemental sulphur.

12. A method according to claim 1, wherein the sulphur is in the form of a sulphur-containing organic covalent compound.

13. A method according to claim 12, wherein the sulphur-containing covalent compound is diphenyl sulphide or thiodipropionic acid.

14. A method according to claim 1, wherein the sulphur is present in the reaction system in an amount of 18 to 30 parts per million (ppm).

15. A method according to claim 14, wherein the sulphur is present in the reaction system in an amount of 20 to 24 ppm.

16. A method according to claim 1, wherein the sodium carbonate is added to the compound to be dehydrogenated and any reaction medium as a solid.

17. A method according to claim 16, wherein the sodium carbonate is added to the compound to be dehydrogenated and any reaction medium as anhydrous sodium carbonate.

18. A method according to claim 1, wherein the sodium carbonate is present in the reaction system in an amount (calculated as anhydrous sodium carbonate) of 0.5 to 1.5% by weight.

19. The method according to claim 1 in which the heating of the compound to be dehydrogenated is carried out in a solvent at a refluxing temperature.

* * * * *